(12) United States Patent
Yin et al.

(10) Patent No.: US 7,327,445 B2
(45) Date of Patent: Feb. 5, 2008

(54) ENHANCED SURFACE PLASMON RESONANCE SENSOR USING GOOS-HÄNCHEN EFFECT

(75) Inventors: Xiaobo Yin, Palo Alto, CA (US); Lambertus Hesselink, Atherton, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 34 days.

(21) Appl. No.: 11/480,278

(22) Filed: Jun. 30, 2006

(65) Prior Publication Data
US 2007/0159633 A1    Jul. 12, 2007

Related U.S. Application Data

(60) Provisional application No. 60/696,182, filed on Jun. 30, 2005.

(51) Int. Cl.
*G01N 21/41* (2006.01)
(52) U.S. Cl. .................................. 356/128; 356/135
(58) Field of Classification Search ............ 356/128, 356/132, 134, 135
See application file for complete search history.

(56) References Cited

U.S. PATENT DOCUMENTS 5,237,392 A * 8/1993 Hickel et al. ............... 356/630
5,633,724 A   5/1997 King et al. ................. 356/445

OTHER PUBLICATIONS

Declercq, Nico et. al. "Theoretical verification of the backward displacement of waves reflected from an interface having superimposed periodicity" (2003) Applied Physics Letters, vol. 82 No. 15.

Birman, Joseph et. al. "Prediction of a Resonance-Enhanced Laser-Beam Displacement at Total Internal Reflection in Semiconductors" (1983) Physical Review Letters vol. 50 No. 21.

Pfleghaar, E. et. al. "Quantitative Investigation of the Effect of Resonant Absorbers on the Goos-Hanchen Shift" (1983) Physical Review Letters, vol. 70 No. 15.

Berman, P.R. Goos Hanchen in negatively refractive media (2002) Physical Review E66, 067603, pp. 067603-1-067603-3.

(Continued)

*Primary Examiner*—Roy M. Punnoose
(74) *Attorney, Agent, or Firm*—Lumen Intellectual Property Services, Inc.

(57) ABSTRACT

An improved surface plasmon resonance (SPR) sensor is provided based on direct measurement of the Goos-Hänchen effect. Sensor sensitivity is enhanced by selecting the thickness of the metallic layer of the SPR sensor to be close to a critical thickness $d_{cr}$ where the effect of the surface plasmon resonance on the Goos-Hänchen shift is most pronounced. Overall sensor sensitivity is surprisingly found to improve with this approach, even though the measurement is based on a second order effect (i.e., the Goos-Hänchen shift) instead of the first order reflectance change measured in conventional SPR sensor approaches. The invention is also applicable to sensors based on measurements of other non-specular reflection parameters, such as temporal shifts, frequency shifts, and/or angular shifts.

23 Claims, 6 Drawing Sheets

OTHER PUBLICATIONS

Nenninger, G.G. et. al. "Long-range surface plasmons for high-resolution surface plasmon resonance sensors" (2001) Elesevier Science B74, pp. 145-151.

Abbate, G. et. al. "Observation of lateral displacement of an optical beam enhanced by surfaces plasmon excitation" (1988) Journal of Modern Optics, vol. 35 No. 7, pp. 1257-1262.

Bonnet, Christopher et. al. "Measurement of positive and negative Goos-Hanchen effects for metallic gratings near Wood anomalies" (2001) The Optical Society vol. 26 No. 10, pp. 666-668.

Hashimoto, Takahuru et. al. "Optical heterodyne sensor using the Goos-Hanchen shift" (1989) The Optical Society, vol. 14 No. 17, pp. 913-915.

* cited by examiner

ENHANCED SURFACE PLASMON RESONANCE SENSOR USING GOOS-HÄNCHEN EFFECT

CROSS REFERENCE TO RELATED APPLICATIONS

This application claims the benefit of U.S. provisional application 60/696,182, filed on Jun. 30, 2005, entitled "Enhanced Surface Plasmon Resonance Sensor Using Goos-Hänchen Effect", and hereby incorporated by reference in its entirety.

FIELD OF THE INVENTION

This invention relates to optical measurement, and more specifically to surface plasmon resonance sensors.

BACKGROUND

In the past few years, surface plasmon resonance (SPR) sensors have become a standard analytical tool for various applications such as life sciences applications, pharmaceutical applications, thin-film metrology and bio-chemical sensors. An SPR sensor typically includes a glass prism having a thin metallic layer deposited on a prism face. The active interface (i.e., sensing interface) of the SPR sensor is the exposed surface of the metallic layer.

In operation, light is totally internally reflected within the prism from the metal-coated surface of the prism, which causes an evanescent optical wave to penetrate into the metallic layer. This evanescent wave can couple to and excite a propagating surface plasmon wave at the sensing interface. Such coupling to the surface plasmon wave can be observed as a reduction in the internally reflected beam power, since the power required to excite the surface plasmon wave comes from this beam. The efficiency with which power is transferred between the incident beam and the surface plasmon wave depends on how nearly a resonance condition is satisfied (i.e., the amount of detuning from resonance). For the on-resonance condition (i.e., detuning=0), power transfer is maximal, and as the magnitude of the detuning increases, power transfer decreases.

In practice, this resonance can be probed by monitoring reflected power as the incident beam angle is varied, or as the incident wavelength is varied, since varying either of these parameters can alter the detuning. In either case, a significant dip in reflectance is observed when passing through the resonance. The particular wavelength (or incident angle) at which resonance occurs is a sensitive function of conditions at the sensing interface, since these conditions influence the properties of the surface plasmon wave. In particular, the resonance is a sensitive function of the refractive index of an analyte in contact with the sensing interface on the metallic layer. As an alternative to measuring the resonant angle (or wavelength, the reflectance can be monitored for a fixed angle of incidence and wavelength as the analyte varies. Typical sensitivities for conventional SPR sensors are on the order of $10^{-5}$ to $10^{-6}$ refractive index units (RIU).

As a first approximation, total internal reflection is a specular reflection process that behaves as expected from geometrical optics. However, non-specular effects in total reflection are known to occur, although these effects tend to be quite small and are often regarded as negligible in practice. One such non-specular effect is the Goos-Hänchen (GH) effect, which is a lateral spatial shift of the reflected beam away from the position expected from geometrical considerations. This effect was first directly measured in 1947 in a difficult experiment where a beam shift on the order of an optical wavelength per reflection was directly measured in the pre-laser era. Multiple reflections were performed in order to increase the observed effect. Indirect measurements of quantities related to the GH effect (such as reflective phase shifts) are sometimes also referred to as measurements of the Goos-Hänchen effect, although this usage can be misleading because such measurements are typically much easier than direct GH measurements. For example, Hashimoto et al. in an article entitled "Optical heterodyne sensor using the Goos-Hänchen shift" (Opt. Lett. 14(17) 913-915 1989) consider a sensor using multiple total reflections that is sensitive to the difference in reflective phase shift between s and p polarized light. Here also, multiple total reflections are performed in order to increase the measured signal.

Although the GH effect typically provides a lateral shift on the order of an optical wavelength, there have been demonstrations of an enhanced GH effect in certain circumstances. An enhanced GH effect has been observed in reflection or total reflection from structures having a surface plasmon resonance. For example, Bonnet et al. investigate large positive and negative GH shifts from metallic gratings in an article entitled "Measurement of positive and negative Goos-Hanchen effects for metallic gratings near Wood anomalies" (Opt. Lett. 26(10) 666-668 2001). An SPR enhanced GH effect in a prism TIR geometry is considered by Abbate et al. in an article entitled "Observation of lateral displacement of an optical beam enhanced by surface plasmon excitation" (J. Mod. Opt. 35(7) 1257-1262 1988). In these articles, lateral shifts on the order of 10-100 λ are observed.

Various approaches have been considered for improving the sensitivity of SPR sensors. For example, the use of long range surface plasmons is considered by Nenninger et al. in an article entitled "Long-range surface plasmons for high-resolution surface plasmon resonance sensors" (Sensors and Actuators B 74 145-151 2001). Long range surface plasmons are coupled surface plasmon waves propagating on opposite interfaces of a thin metallic layer. Other approaches that have been considered include performing differential measurements, fabricating resonant structures such as nanoparticles, and the use of phase-sensitive techniques such as ellipsometry and interferometric detection. Of these approaches, phase sensitive techniques appear to provide the best sensitivity, although such techniques also and undesirably introduce significant additional complexity into the sensor.

Accordingly, it would be an advance in the art to provide an SPR sensor having improved sensitivity and/or reduced complexity compared to conventional SPR sensors.

SUMMARY

An improved surface plasmon resonance (SPR) sensor is provided based on direct measurement of the Goos-Hänchen effect. Sensor sensitivity is enhanced by selecting the thickness of the metallic layer of the SPR sensor to be close to a critical thickness $d_{cr}$ where the effect of the surface plasmon resonance on the Goos-Hänchen shift is most pronounced. Overall sensor sensitivity is surprisingly found to improve with this approach, even though the measurement is based on a second order effect (i.e., the Goos-Hänchen shift) instead of the first order reflectance change measured in conventional SPR sensor approaches. The invention is also applicable to sensors based on measurements of other non-specular reflection parameters, such as temporal shifts, frequency shifts, and/or angular shifts.

DETAILED DESCRIPTION

Figure 1:
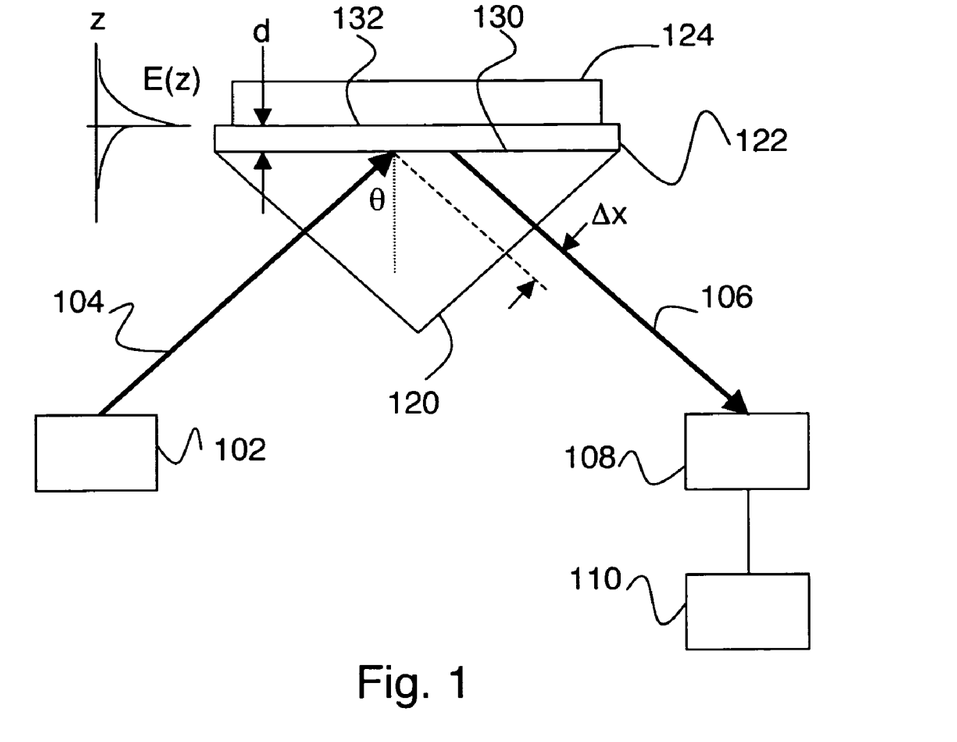
FIG. 1 shows an embodiment of the invention.

FIG. 1 shows an embodiment of the invention. An optical source 102 provides an input beam of optical radiation 104. Typically, input beam 104 is substantially monochromatic at a fixed or tunable wavelength $\lambda$. Input beam 104 propagates within a prism 120, and is internally reflected within prism 120 from a surface 130 of prism 120 to provide an output beam 106. A metallic layer 122 is disposed on surface 130 of prism 120. Metallic layer 122 makes contact with an analyte 124 at a sensing interface 132. Sensing interface 132 is thus the surface of metallic layer 122 that faces away from prism 120.

Sensing interface 132 supports propagation of a surface plasmon wave. Such a wave has a field distribution that exponentially decreases as the distance from the sensing interface increases, as shown in the E(z) vs. z sketch of FIG. 1. In practicing the invention, it is important that the thickness d of metallic layer 122 be selected to enhance the effect of the surface plasmon resonance on the Goos-Hänchen shift. More specifically, let metallic layer 122 have a complex refractive index of $n+j\kappa$, and define a critical thickness $d_{cr}$ given by $$d_{cr} = \frac{\lambda}{4\pi\kappa} \ln \frac{2\kappa}{n}.$$

The thickness of metallic layer 122 is selected such that $0.5\, d_{cr} \leq d \leq 1.5\, d_{cr}$, and more preferably such that $0.85\, d_{cr} \leq d \leq 1.15\, d_{cr}$.

Output beam 106 is received by a detection system 108 which can provide a measurement of the beam shift $\Delta x$ (i.e., the Goos-Hänchen shift) of output beam 106 relative to a geometrical intersection point of input beam 104 and surface 130. Thus a beam shift $\Delta x=0$ corresponds to the case of ideal geometrical reflection. Non-zero beam shifts $\Delta x$ can either be positive (as shown on FIG. 1) or negative. Negative beam shifts can arise in cases where input beam 104 couples to a backward propagating surface plasmon wave that propagates from right to left along sensing interface 132 on FIG. 1. Although any technique can be employed to measure the spatial shift $\Delta x$ of output beam 106, in a preferred embodiment a position-sensitive detector is employed having two photocurrent outputs, where the differential current of the two outputs is proportional to the output beam position on the position-sensitive detector. Such position sensitive detectors are readily available commercially.

The measured beam shift provided by the detection system is provided to a processor 110 for determining a refractive index of an analyte 124 from the beam shift. As shown in more detail below, the beam shift $\Delta x$ depends on a detuning from a surface plasmon resonance condition. Thus the arrangement of FIG. 1 can be regarded as an SPR sensor where the effect of analyte refractive index on the surface plasmon resonance is sensed by measuring changes in the Goos-Hänchen shift $\Delta x$ as opposed to the conventional SPR sensor approach of measuring changes in reflectance. A surprising discovery of the present invention is that SPR sensor sensitivity in terms of minimum resolvable change in refractive index can be significantly improved by measuring $\Delta x$ in accordance with the invention instead of measuring reflectance.

More specifically, one would generally expect an SPR sensor based on a second order effect (such as the Goos-Hänchen shift) to be less sensitive than an SPR sensor based on a first order effect (such as reflectance change). Investigations by the present inventors have identified two key factors contributing to the surprising result that the second order measurement can outperform the first order measurement. The first factor is the appropriate selection of metallic layer thickness, as described above. This is important to enhance the effect of the surface plasmon resonance on the measured beam shifts, thereby increasing detector sensitivity. The second factor is that the Goos-Hänchen shift has been found to be more sensitive to changes in detuning from the surface plasmon resonance condition than the reflectance. This increased sensitivity to detuning also provides a corresponding improvement in detector sensitivity.

The ability of input beam 104 to couple to the surface plasmon wave at sensing interface 132 is polarization-dependent. More specifically, if input beam 104 is TE polarized, coupling to the surface plasmon wave cannot occur, while if input beam 104 is TM polarized, coupling to the surface plasmon wave can occur. Thus it is preferred for source 102 to provide polarization modulation of input beam 104. When input beam 104 is TE polarized, it provides a reference output beam 106 that is not affected by the surface plasmon wave, and thus has a beam shift that is substantially independent of the refractive index of analyte 124. When input beam 104 is TM polarized, it provides an output beam 106 that couples to the surface plasmon wave, and thus has a beam shift that is dependent on the refractive index of analyte 124. In this manner, the effect of the analyte refractive index can be determined from a measurement of the TM beam shift relative to the TE beam shift.

Figure 2:
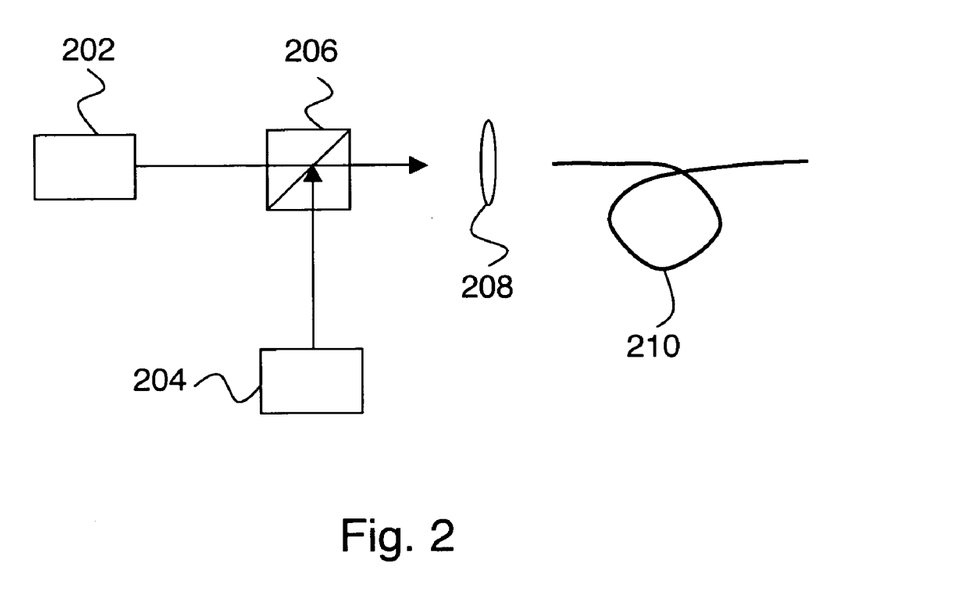
FIG. 2 shows an optical source suitable for use with the invention.

FIG. 2 shows a preferred source for polarization modulation. Two laser diodes 202 and 204, one having TE polarized output and the other having TM polarized output, provide light to a polarizing beam splitter 206. In this geometry, beam splitter 206 functions as a combiner and provides radiation to coupling optics 208 (e.g., a lens) which couples the combined radiation to a single-mode polarization maintaining fiber 210. Input beam 104 is emitted from the other end of fiber 210. Polarization modulation is accomplished by selectively driving the two laser diodes in a complementary manner, so that when diode 202 is on, diode 204 is off, and vice versa. By coupling both laser diodes to the same single mode fiber, potential errors due to different laser diode beam parameters (e.g., different beam pointing directions) are eliminated. In practice, a polarization modulation depth of greater than 15 dB has been obtained with this technique. Although this technique for polarization modulation is preferred due to its simplicity in practice, any other method of polarization modulation (e.g., using an electro-optic modulator, etc.) is also suitable for practicing the invention.

A further refinement of this modulation technique entails the use of feedback control of the laser diodes to eliminate intensity modulation at the detection system. Such intensity modulation occurs because the TE reflectance tends to be higher than the TM reflectance, and is undesirable because it can interfere with the beam position measurement. The output power of the TE laser diode can be controlled according to the RMS value of the measured intensity modulation in a loop designed to drive this RMS value to zero. This approach (or any other equivalent feedback method) can provide constant total optical power to the detection system.

Figure 3:
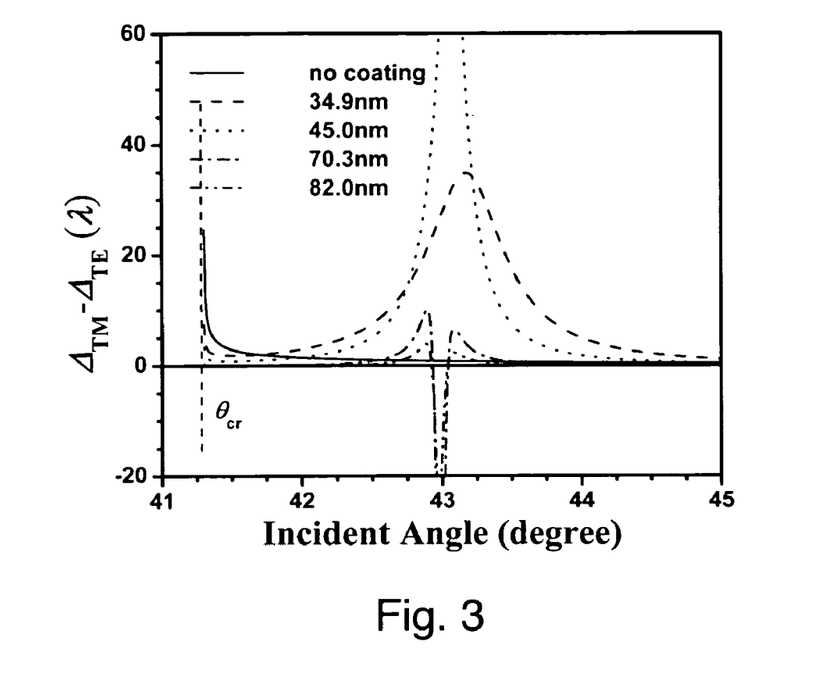
FIG. 3 shows beam shifts measured in an embodiment of the invention.

FIG. 3 shows measured beam shift results from embodiments of the invention. In this example, metallic layer 122 is a silver layer, and prism 120 is a BK7 glass prism. Results for various layer thicknesses d are shown, and for comparison measured results from an uncoated prism are also shown (solid line). Beam shifts are expressed in terms of wavelengths. Input beam 104 is from a HeNe laser ($\lambda$=632.8 nm), and the detuning is varied by altering the angle of incidence. The critical angle for total internal reflection (TIR) is $\theta_c$=41.3°, and the SPR resonance angle is about 42.8°. Since an SPR sensor is operated at or near the SPR resonance condition, the angle of incidence is at or near the SPR resonance angle. In most cases (as in this example), this means that the angle of incidence is greater than the TIR angle. However, it is possible for the SPR resonance angle to be at or slightly below the TIR angle, and in such cases the angle of incidence would also be at or slightly below the TIR angle.

The sensitivity of the TE-TM relative beam shift to changes in detuning (i.e., angle of incidence) is clearly seen on FIG. 3. For metallic layer thicknesses less than about 60 nm, the beam shift is an increasing function of layer thickness. Large shifts are observed (e.g., 50 $\lambda$ or more for a 45 nm thick film). For layer thicknesses greater than about 60 nm, negative shifts are observed. In this example, the critical layer thickness is 59 nm, and it is clearly preferable for the layer thickness to be at or near the critical layer thickness for maximum sensitivity. As indicated above, varying the angle of incidence and varying the incident wavelength are two ways of altering the detuning from the SPR condition. Thus results analogous to those shown on FIG. 3 would also be obtained if the incident wavelength were varied at a fixed angle of incidence.

Figure 4:
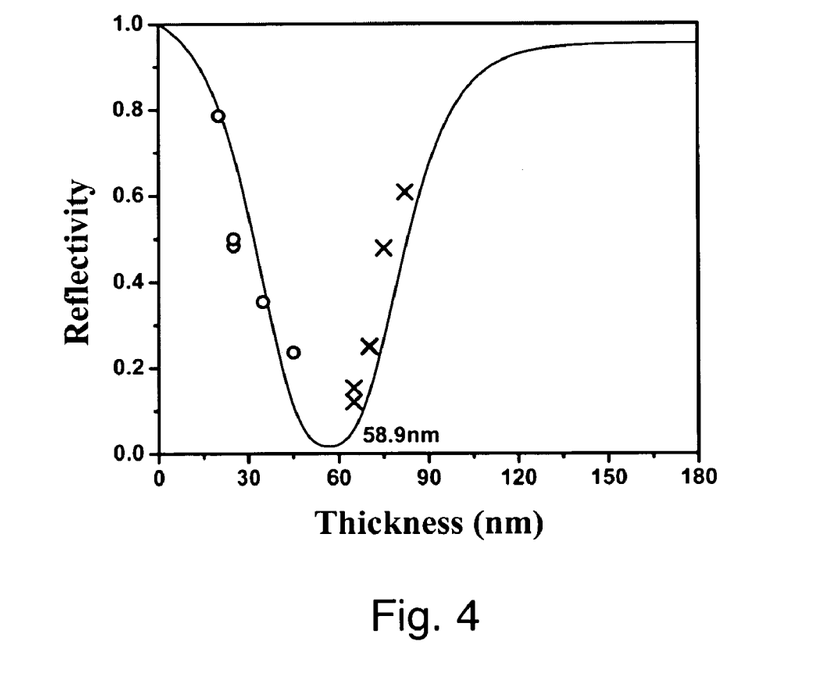
FIG. 4 shows the thickness dependence of the TM reflectivity observed in an embodiment of the invention.

FIG. 4 shows the thickness dependence of the TM reflectance together with experimental data points (o positive beam shift; x negative beam shift) for the example of FIG. 3. The reflectance is seen to be minimal at the critical thickness, and it is also apparent that the sign of the maximum beam shift depends on whether the layer thickness is greater than or less than the critical thickness.

Figure 5:
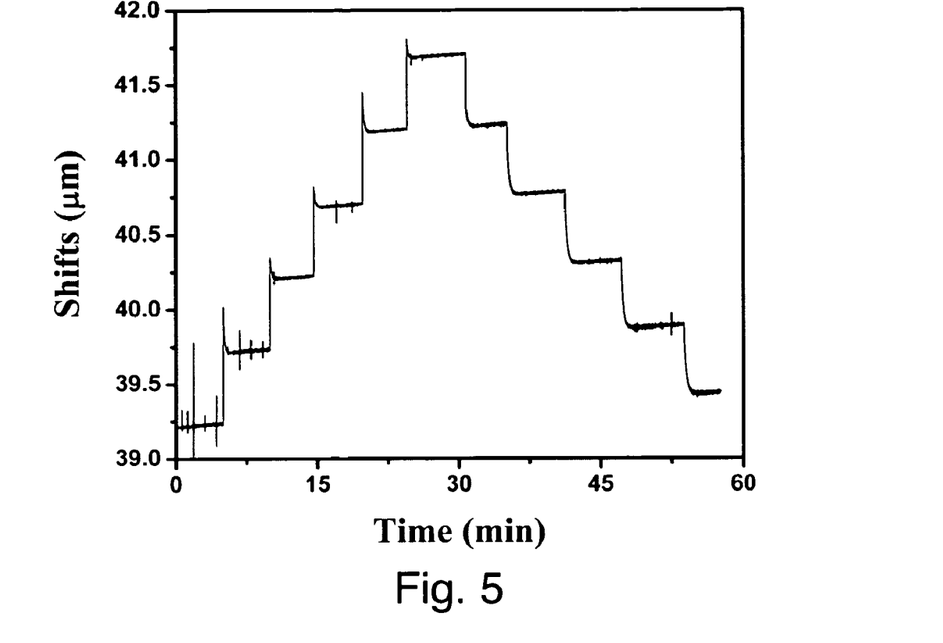
FIG. 5 shows measured beam shifts from an embodiment of the invention as the analyte is varied.

FIG. 5 shows a typical real-time record of measured beam shifts where the analyte is an aqueous solution of sodium chloride with varying concentration. Here 980 nm light is used in combination with a 42 nm thick ($\approx d_{cr}$ at this wavelength) Au metallic layer. Sensing surface 132 is incorporated into the interior surface of a suitable fluidic cell for this measurement. Each step on FIG. 5 represents a concentration change of $10^{-3}$ M.

Figure 6:
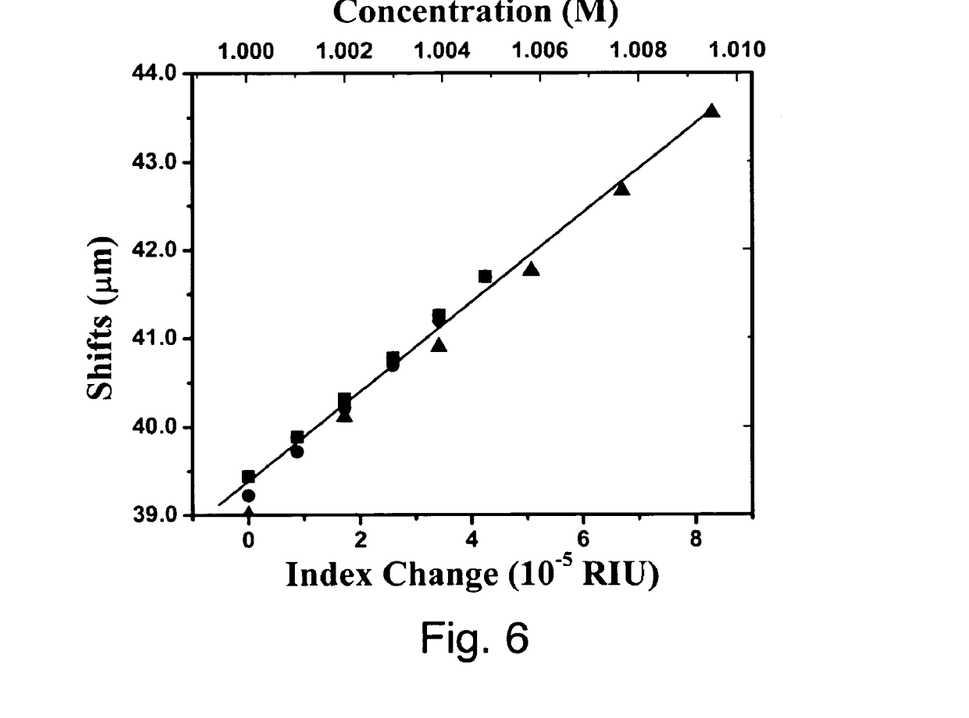
FIG. 6 shows a measured curve of beam shift vs. index change (or analyte concentration).

FIG. 6 shows results from several experimental runs of the kind shown in FIG. 5. The measured sensitivity is $1.82 \times 10^{-8}$ RIU/nm, where 1 RIU is one refractive index unit (i.e. a change of 1 in the refractive index). In this experiment, the position resolution was on the order of 20 nm, which provides an index resolution of about $4 \times 10^{-7}$ RIU. This resolution is a substantial improvement compared to conventional SPR sensors ($10^{-5}$ to $10^{-6}$ RIU). Further improvements in resolution can be realized by improving the beam position resolution to the sub-nm level, which can be accomplished with known laser position detection methods. For example, an optical lens system can be employed to magnify the beam displacement prior to detection. The result of FIG. 6 can be regarded as a calibration curve establishing a relation between measured beam shift, refractive index and concentration.

The preceding description is by way of example as opposed to limitation, since the principles of the invention are also applicable to numerous other situations.

Figure 7:
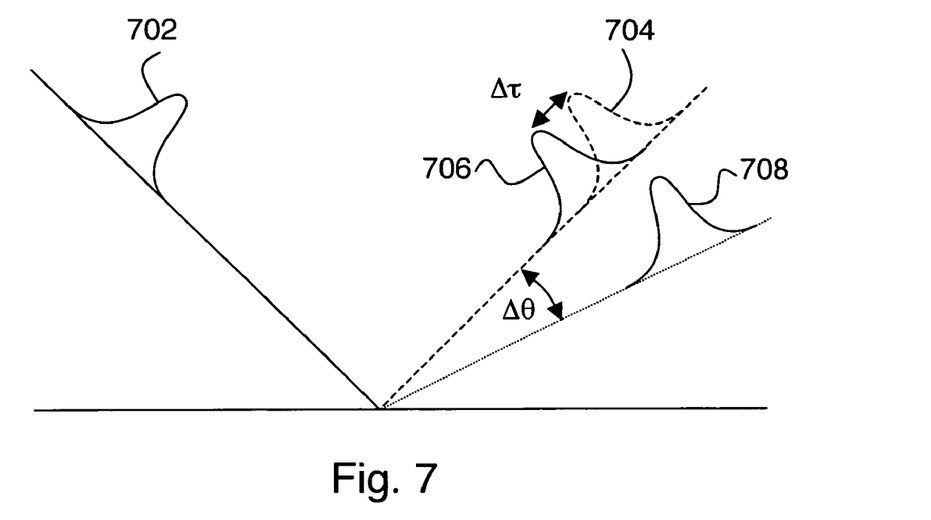
FIG. 7 shows effects of some non-specular reflection parameters.
Figure 8A:
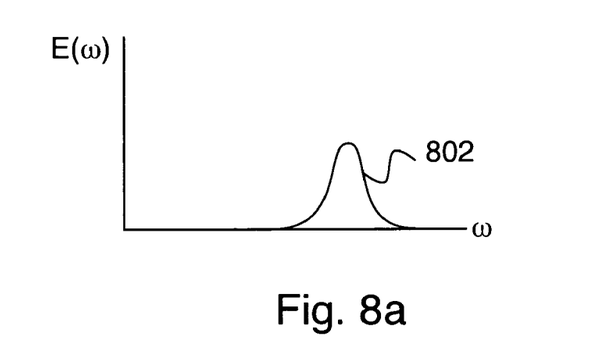
FIG. 8 shows the effect of a non-specular reflection frequency shift.
Figure 8B:
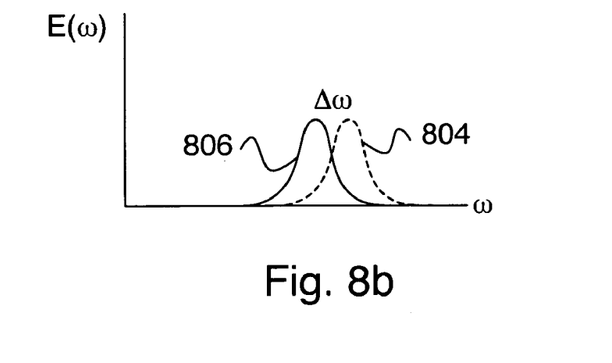

For example, the Goos-Hänchen shift is one example of a non-specular reflection effect. The invention can also be practiced in connection with other non-specular reflection effects. FIG. 7 shows two such non-specular effects relative to an incident pulse of optical radiation 702. A reflected pulse 708 can propagate along a path that is separated from the geometrically expected path by an angular shift $\Delta\theta$. Similarly, a reflected pulse 706 can be separated from a nominal pulse position 704 by a temporal shift $\Delta\tau$, where the nominal position is the position that would be expected assuming geometrical propagation. FIG. 8 shows a third non-specular reflection effect, where an input pulse has a spectrum 802, and a reflected pulse 806 is shifted in frequency by $\Delta\omega$ compared to the reflected pulse 804 that would be obtained without dispersion. As with the Goos-Hänchen shift, these angular, temporal and frequency shifts can occur with either sign. The invention therefore relates to measuring one or more non-specular reflection parameters to sense refractive index in an SPR sensor. Such parameters include lateral spatial shifts, angular shifts, temporal shifts and frequency shifts of the output beam.

Figure 9:
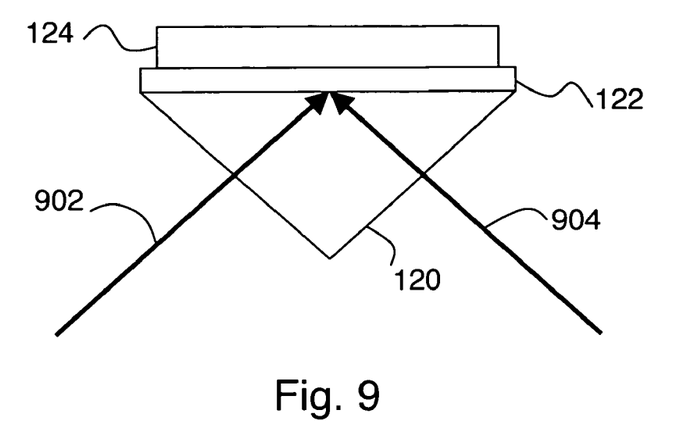
FIG. 9 shows an embodiment of the invention where two source beams are employed to generate a fringe pattern at the sensing interface.

FIG. 9 shows another embodiment of the invention. In this example, two input beams 902 and 904 are provided to the SPR sensor that interfere at the prism surface to create a fringe pattern. The fringe pattern produces localized intensity variations that may be useful for obtaining localized information from the analyte. The fringe pattern can also be employed to modify interactions between the incident waves and the surface plasmon wave(s).

Figure 10:
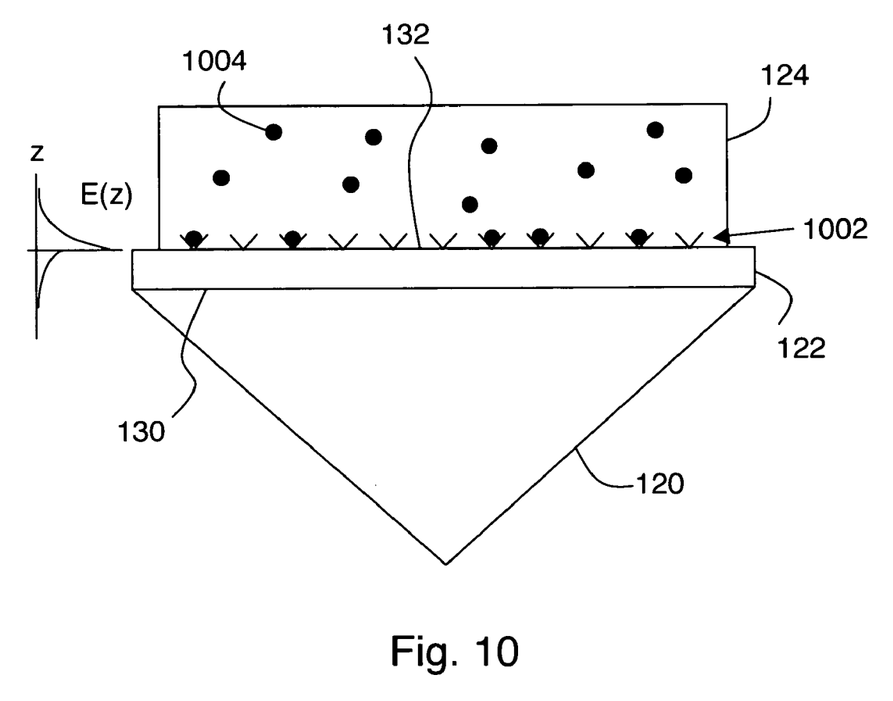
FIG. 10 shows an embodiment of the invention where a chemical binding agent is disposed at the sensing interface.

FIG. 10 shows yet another embodiment of the invention. In this example, a chemical binding agent 1002 is disposed at sensing interface 132. Binding agent 1002 is capable of binding species 1004 present in analyte 124. The SPR sensor of FIG. 10 is selectively responsive to the concentration of bound species 1004 at sensing interface 132 due to the exponential decay of the surface plasmon wave within analyte 124. In this manner, the enhanced SPR sensitivity provided by the present invention can be combined with the chemical selectivity provided by binding agent 1002 to provide a highly sensitive and highly specific measurement of species 1004.

Figure 11:
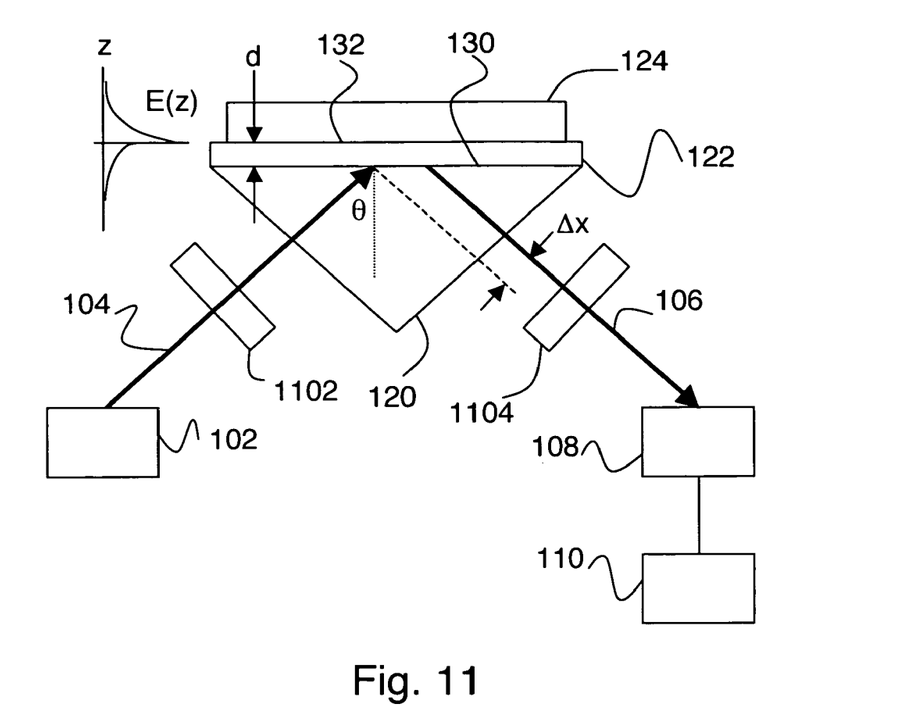
FIG. 11 shows an embodiment of the invention having input and output polarizers, which is suitable for performing weak quantum-mechanical measurements.

The invention is also applicable for making weak quantum mechanical (QM) measurements, as first considered by Aharonov, Albert and Vaidman (Phys. Rev. Lett. 60 1351 1988). FIG. 11 shows an embodiment of the invention suitable for performing a weak QM measurement. FIG. 11 is similar to FIG. 1, expect that input and output polarizers 1102 and 1104 respectively are added on FIG. 11. These polarizers serve to preselect the input and output states of polarization. Preferably, the input and output state of polarization is selected to be TM to make use of the surface plasmon resonance enhancement. Although these polarizers are shown as separate elements on FIG. 11, they can also be integrated with source 102 and/or detector system 108.

For an incident Gaussian wave packet having spatial and temporal half widths $\sigma_\rho$ and $\sigma_t$ respectively, the reflected wave packet in the weak measurement formalism is given by $$\phi_f(k_p, \omega) = \exp\left\{\frac{ik_\rho \text{Re}(W_\rho) + i\omega \text{Re}(W_t) - k_\rho + 2\sigma_\rho^2 \text{Im}(W_\rho)}{4\sigma_\rho^2} - \frac{\omega + 2\sigma_t^2 \text{Im}(W_t)}{4\sigma_t^2}\right\}. \quad (1)$$

Here the weak values $W_\rho$ and $W_t$ are expectation values of weak operators $\hat{W}_\rho$ and $\hat{W}_t$ given by $W_\rho = \langle \psi_f | \hat{W}_\rho | \psi_i \rangle / \langle \psi_f | \psi_i \rangle$ and $W_t = \langle \psi_f | \hat{W}_t | \psi_i \rangle / \langle \psi_f | \psi_i \rangle$, and the initial and final states $\psi_i$ and $\psi_f$ include the preselected input and output polarizations respectively. The weak operators $\hat{W}_\rho$ and $\hat{W}_t$ are related to the unitary reflection operator $\hat{U}(k_\rho, \omega)$ as follows:

$$\hat{W}_t = -i(\partial_\omega \hat{U})\hat{U}^\dagger|_{\omega=\omega_0}$$

$$\hat{W}_\rho = -i(\partial_{k_\rho} \hat{U})\hat{U}^\dagger|_{k_\rho=k_0} \quad (2)$$

where $\omega_0$ and $k_0$ are the center frequency and center transverse wave vector respectively of the incident Gaussian wave packet.

Eqs. 1 and 2 provide a unified description of the four non-specular reflection effects described above. More specifically, the real part of $W_\rho$ relates to the Goos-Hänchen shift, and the imaginary part of $W_\rho$ relates to the angular shift shown on FIG. 7. The real part of $W_t$ relates to the temporal shift shown on FIG. 7, and the imaginary part of $W_t$ relates to the frequency shift shown on FIGS. 8a-b. Weak QM measurements of any of these parameters can be enhanced according to principles of the invention by exploiting the surface plasmon resonance as described above.

The preceding description refers to measurements of the refractive index of the analyte. Such measurements can be absolute measurements of the refractive index, or they can be measurements of changes in the refractive index (e.g., relative measurements), depending on the needs of the application being considered.

Figure 12:
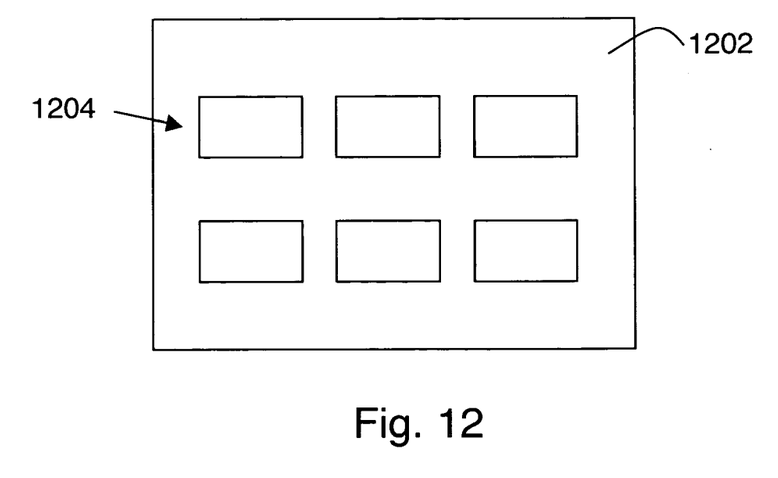
FIG. 12 shows a top view of a sensor array according to the invention.

Sensors according to the present invention can be individual devices as described above, or they can be sensor arrays, where multiple analytes are measured in accordance with principles of the invention. For example, an analyte array can be disposed on the sensing interface, where each element of the analyte array can be separately optically probed by measuring the beam shift when the input beam is directed to the element. Such optical probing can be performed sequentially or in parallel. FIG. 12 shows a top view of such a sensor, where multiple laterally separated analytes are disposed on a sensing interface 1202. Here sensing interface 1202 corresponds to sensing interface 132 of FIG. 1.

Sensors according to the invention can also be partially or completely integrated. For example, a sensor head unit including the prism, the metallic layer and a cell for holding the analyte is one possible partially integrated configuration. Such head units can have small size and/or low cost, and may even be disposable.

The invention claimed is:

1. Apparatus for measuring the refractive index of an analyte, the apparatus comprising:
   an optical source capable of providing an input beam of optical radiation at a wavelength $\lambda$;
   a prism having a surface capable of receiving and internally reflecting the input beam within the prism to provide an output beam;
   a metallic layer on the surface of the prism, wherein a sensing interface of the metallic layer facing away from the surface of the prism is in contact with the analyte, wherein the sensing interface supports propagation of a surface plasmon wave, wherein the metallic layer has a complex refractive index n+jκ, wherein a critical thickness $d_{cr}$ is given by $$d_{cr} = \frac{\lambda}{4\pi\kappa}\ln\frac{2\kappa}{n},$$

and wherein a thickness d of the metallic layer is selected such that $0.5\, d_{cr} \leq d \leq 1.5\, d_{cr}$, wherein, n is the real part of the complex refractive index and jκ is the imaginary part of the complex refractive index;
   a detection system capable of receiving the output beam and providing a measurement of at least one non-specular reflection parameter of the output beam, wherein the non-specular reflection parameter depends in part on a detuning from a surface plasmon wave resonance condition;
   a processor capable of determining a refractive index of the analyte from the measured non-specular reflection parameter.

2. The apparatus of claim 1, wherein a state of polarization of said input beam is modulated between a first state of polarization that is substantially TM with respect to said surface and a second state of polarization that is substantially TE with respect to said surface.

3. The apparatus of claim 1, wherein said non-specular reflection parameter is selected from the group consisting of a lateral spatial shift of said output beam; an angular shift of said output beam; a temporal shift of said output beam; and a frequency shift of said output beam.

4. The apparatus of claim 3, wherein said non-specular reflection parameter is a lateral spatial shift of said output beam.

5. The apparatus of claim 4, wherein said lateral spatial shift is positive with respect to a geometrical intersection point of said input beam and said surface.

6. The apparatus of claim 4, wherein said lateral spatial shift is negative with respect to a geometrical intersection point of said input beam and said surface.

7. The apparatus of claim 4, wherein said detection system comprises a position sensitive detector providing a differential photocurrent output depending on a position of said output beam.

8. The apparatus of claim 1, wherein an angle of incidence of said input beam at said surface is greater than a critical angle for total internal reflection.

9. The apparatus of claim 1, wherein said thickness d of said metallic layer is selected such that $0.85\, d_{cr} \leq d \leq 1.15\, d_{cr}$.

10. The apparatus of claim 1, wherein two or more of said optical source, said prism, said metallic layer, said detection system, and said processor are integrated into a single unit.

11. A method for measuring the refractive index of an analyte, the method comprising:
providing a first input beam of optical radiation at a wavelength λ;
directing the first input beam to a surface of a prism, where the first input beam is internally reflected within the prism to provide an output beam;
providing a metallic layer on the surface of the prism, wherein a sensing interface of the metallic layer facing away from the surface of the prism is in contact with the analyte, wherein the sensing interface supports propagation of a surface plasmon wave, wherein the metallic layer has a complex refractive index n+jκ, wherein a critical thickness $d_{cr}$ is given by $$d_{cr} = \frac{\lambda}{4\pi\kappa}\ln\frac{2\kappa}{n},$$

and wherein a thickness d of the metallic layer is selected such that $0.5\, d_{cr} \leq d \leq 1.5\, d_{cr}$, wherein, n is the real part of the complex refractive index and jκ is the imaginary part of the complex refractive index;
measuring at least one non-specular reflection parameter of the output beam, wherein the non-specular reflection parameter depends in part on a detuning from a surface plasmon wave resonance condition;
determining a refractive index of the analyte from the measured non-specular reflection parameter.

12. The method of claim 11, further comprising modulating a state of polarization of said input beam between a first state of polarization that is substantially TM with respect to said surface and a second state of polarization that is substantially TE with respect to said surface.

13. The method of claim 11, wherein said non-specular reflection parameter is selected from the group consisting of a lateral spatial shift of said output beam; an angular shift of said output beam; a temporal shift of said output beam; and a frequency shift of said output beam.

14. The method of claim 11, further comprising providing a second input beam and directing the second input beam to said surface of said prism, wherein said first and second input beams interfere at said surface to provide a fringe pattern.

15. The method of claim 11, further comprising determining a calibration relation between said non-specular reflection parameter and a refractive index of said analyte using one or more calibration analytes having known refractive indices.

16. The method of claim 11, further comprising providing one or more chemical binding agents at said sensing interface and determining concentrations of one or more bound species at said sensing interface from said refractive index.

17. The method of claim 11, wherein said input beam is provided with a predetermined input state of polarization, and further comprising passing said output beam through an output polarizer providing a predetermined output state of polarization, whereby a weak quantum-mechanical measurement of an operator associated with said output beam is provided.

18. The method of claim 11, wherein an angle of incidence of said input beam at said surface is greater than a critical angle for total internal reflection.

19. The method of claim 11, wherein said thickness d of said metallic layer is selected such that $0.85\, d_{cr} \leq d \leq 1.15\, d_{cr}$.

20. The method of claim 11, wherein said determining a refractive index provides an absolute refractive index determination.

21. The method of claim 11, wherein said determining a refractive index provides a relative refractive index determination.

22. A method for measuring the refractive index of two or more analytes, the method comprising:
disposing each analyte on a common sensing interface, wherein each analyte occupies a distinct region of the common sensing interface;
measuring the refractive index of each analyte according to the method of claim 11;
wherein said sensing interface for each of the analytes is the common sensing interface.

23. Apparatus for measuring the refractive index of an analyte, the apparatus comprising:
means for providing an input beam of optical radiation at a wavelength λ;
means for receiving and internally reflecting the input beam at a surface to provide an output beam;
a metallic layer on the surface, wherein a sensing interface of the metallic layer facing away from the surface is in contact with the analyte, wherein the sensing interface supports propagation of a surface plasmon wave, wherein the metallic layer has a complex refractive index n+jκ, wherein a critical thickness $d_{cr}$ is given by $$d_{cr} = \frac{\lambda}{4\pi\kappa}\ln\frac{2\kappa}{n},$$

and wherein a thickness d of the metallic layer is selected such that $0.5\, d_{cr} \leq d \leq 1.5\, d_{cr}$, wherein, n is the real part of the complex refractive index and jκ k is the imaginary part of the complex refractive index;
means for receiving the output beam and providing a measurement of at least one non-specular reflection parameter of the output beam, wherein the non-specular reflection parameter depends in part on a detuning from a surface plasmon wave resonance condition;
means for determining a refractive index of the analyte from the measured non-specular reflection parameter.

* * * * *